United States Patent
Koyama et al.

(10) Patent No.: US 7,186,544 B2
(45) Date of Patent: Mar. 6, 2007

(54) AGENTS FOR PROMOTING FATTENING OF ANIMALS AND METHOD OF PROMOTING FATTENING

(75) Inventors: Hironari Koyama, Osaka (JP); Masaaki Okada, Osaka (JP)

(73) Assignee: Fuso Chemical Co., Ltd., Osaka (JP)

(*) Notice: Subject to any disclaimer, the term of this patent is extended or adjusted under 35 U.S.C. 154(b) by 0 days.

(21) Appl. No.: 10/769,849

(22) Filed: Feb. 3, 2004

(65) Prior Publication Data

US 2004/0156855 A1    Aug. 12, 2004

Related U.S. Application Data

(62) Division of application No. 10/110,215, filed as application No. PCT/JP00/07237 on Oct. 18, 2000, now Pat. No. 6,718,910.

(30) Foreign Application Priority Data

Oct. 19, 1999    (JP)    .................... 11-296725

(51) Int. Cl.
*A01N 63/00*    (2006.01)

(52) U.S. Cl. ................ 435/252.4; 435/243; 435/252.1; 424/93.4; 426/651

(58) Field of Classification Search ............ 119/51.01; 426/2, 635, 805, 807, 651; 435/243, 252.4, 435/252.1; 424/93.4
See application file for complete search history.

(56) References Cited

U.S. PATENT DOCUMENTS

| | | | |
|---|---|---|---|
| 3,939,275 A * | 2/1976 | Baile et al. ................ 514/535 |
| 4,001,453 A | 1/1977 | Huber et al. | |
| 4,095,000 A | 6/1978 | Brenner | |
| 4,164,568 A | 8/1979 | Bywater | |
| 4,234,599 A | 11/1980 | Van Scott et al. | |
| 4,353,902 A * | 10/1982 | Hedde et al. ............ 514/400 |
| 4,362,710 A | 12/1982 | Watanabe | |
| 4,504,471 A * | 3/1985 | Takagi et al. ............ 514/18 |
| 4,528,197 A | 7/1985 | Blackburn | |
| 4,559,234 A | 12/1985 | Rubin et al. | |
| 4,647,453 A | 3/1987 | Meinser | |
| 4,869,907 A | 9/1989 | Sasagawa | |
| 4,954,355 A | 9/1990 | Haarasilta et al. | |
| 4,960,589 A | 10/1990 | Sasagawa | |
| 5,364,788 A | 11/1994 | Kubo | |
| 5,462,967 A * | 10/1995 | Hayashi ............ 514/547 |
| 5,529,793 A | 6/1996 | Garner et al. | |
| 5,534,271 A | 7/1996 | Ware et al. | |
| 5,549,890 A | 8/1996 | Kubo | |
| 5,997,911 A | 12/1999 | Brinton et al. | |
| 6,387,419 B1 | 5/2002 | Christensen | |
| 6,455,063 B1 | 9/2002 | Rehberger et al. | |
| 6,506,402 B1 | 1/2003 | Winstrom | |

FOREIGN PATENT DOCUMENTS

| | | |
|---|---|---|
| EP | 0 346 908 | 12/1989 |
| EP | 0 385 960 A2 | 9/1990 |
| EP | 0 667 107 | 8/1995 |
| GB | 2 280 091 | 1/1995 |
| JP | 56-121436 | 9/1981 |
| JP | 56-121456 | 9/1981 |
| JP | 1-98446 | 4/1989 |

OTHER PUBLICATIONS

T. Asano, et al., Microbial Ecology in Health and Disease, vol. 7, No. 5, XP-000618273, pp. 247-256, "Effects of Gluconic Acid on Human Faecal Bacterial", Sep. 1, 1994.
Derwent Publications, XP-002223928, AN 1978-71294A, JP 53-098287, Aug. 28, 1978.
Patent Abstracts of Japan, JP 60-164442, Aug. 27, 1985.
Toshihito Asano et al., "Effects of gluconic acid on the human faecal microflora," Microecology and Therapy vol. 23 (1995) pp. 89-93 (Full text).
"Statutory Instrument 1995 No. 3187", The Miscellaneous Food Additives Regulations 1995, http://www.hmso.gov.uk/si/si1995/Uksi_19953187_en_3.htm, pp. 1-6.

* cited by examiner

*Primary Examiner*—Leon Blame Lankford, Jr.
(74) *Attorney, Agent, or Firm*—Oblon, Spivak, McClelland, Maier & Neustadt, P.C.

(57) ABSTRACT

Agents for promoting fattening of animals which contain as the active ingredient(s) at least one member selected from among acids originating in hexoses, non-toxic salts thereof and intramolecular esterification products thereof; and a method of promoting fattening by using these agents.

7 Claims, 1 Drawing Sheet

AGENTS FOR PROMOTING FATTENING OF ANIMALS AND METHOD OF PROMOTING FATTENING

This application is a Division of 10/110,215 Apr. 19, 2002 U.S. Pat. No. 6,718,910 which is a 371 of PCT/JP00/07237 Oct. 18, 2000.

TECHNICAL FIELD

The present invention relates to an agent for promoting the fattening of animals and to a method for promoting the fattening of animals. More precisely, the invention relates to an agent for promoting the fattening of animals, which contains, as an active ingredient, at least one of hexose-derived acids such as typically gluconic acid, and their non-toxic salts and intramolecular ester compounds, and to a method of promoting the fattening of animals by use thereof.

BACKGROUND ART

For promoting the growth of animals such as livestock, antibiotics such as tetracycline and avoparcin have heretofore been used by being added to feed as fattening promoters. However, these antibiotics often induce resistant bacteria through mutation in the body of animals. In addition, they may remain in the body of animals, and the human beings who have eaten the meat of the animals shall inevitably take the antibiotics. As a result, the potency of antibiotics serving as medicines will be thereby lowered.

Recently, therefore, substances except antibiotics have been investigated for fattening promoters for animals. For example, fumaric acid is used as a fattening promoter.

On the other hand, gluconic acid which is one typical example of hexose-derived acids has heretofore been widely used. For example, its intramolecular ester compound, glucono delta lactone is known as a coagulant for tofu (soybean curd); and calcium gluconate is known as a calcium supplement. In addition, sodium gluconate and potassium gluconate have been officially approved as food additives recently and are used in various edibles (International Patent No. WO94/09650).

DISCLOSURE OF THE INVENTION

The inventors of the present invention have tried administering gluconic acid and its derivatives, which are highly safe to living bodies, to animals and analyzing their activity to the living bodies. Having specifically examined their effect in the animal intestines, the inventors have found unexpectedly that they promote the growth of specific enterobacteria in the animals and that the thus-growing enterobacteria significantly increase the production of short-chain fatty acids which are effective for the growth of the living bodies. In addition, the inventors have further found that the production of substances that will be harmful to living bodies is reduced or eliminated.

That is, if hexose-derived acids and their non-toxic salts and intramolecular ester compounds (hereinafter the term "hexose-derived acids" generally includes all these compounds) are administered to animals, *Megasphaera* and *Mitsuokella*, precisely *Megasphaera elsdenii* and *Mitsuokella multiacidus*, among enterobacteria in the animals are specifically proliferated.

On the other hand, as compared with the absence of the hexose derived acids, the production of acetic acid, propionic acid and butyric acid which are short-chain fatty acids is promoted about 2 times, about 4 times and about 8 times more, respectively. At the same time, the production of lactic acid, succinic acid, ammonia and hydrogen sulfide which are reported to have some negative influences such as diarrhea, digestive tract ulcers, lumen acidosis, etc. on living bodies is reduced or eliminated.

Therefore, if the hexose-derived acids are given to animals, the production of short-chain fatty acids is promoted in the living bodies of the animals, and, as a result, the feed efficiency is improved remarkably and the fattening of the animals is thereby accelerated.

BEST MODES OF CARRYING OUT THE INVENTION

Figure 1:
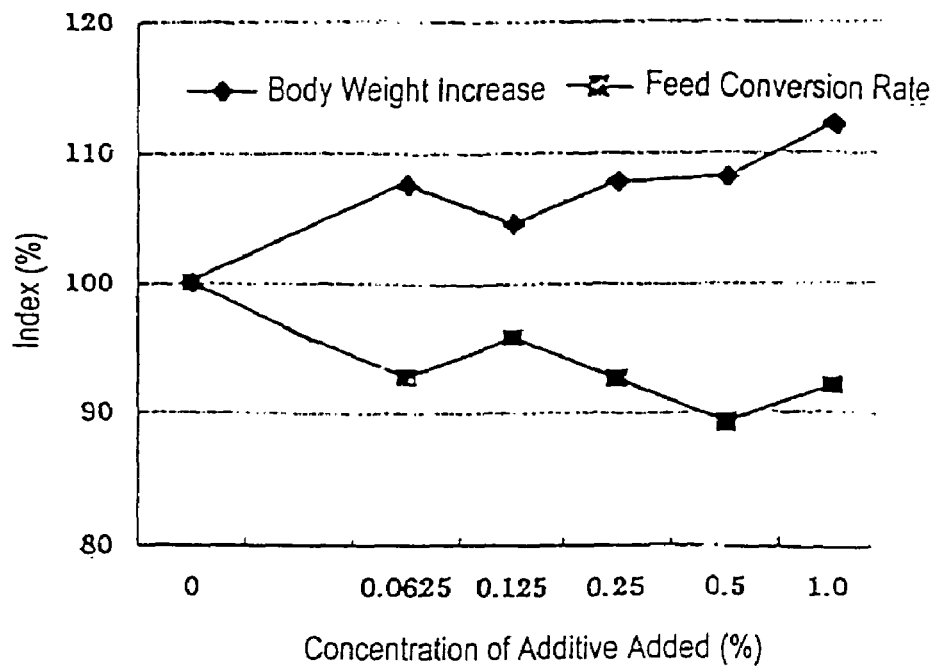
FIG. 1 is a graph showing the results of Test Example 1.

The hexose-derived acids in the invention may be any of D-forms, L-forms or their mixtures. For example, they include saccharic acids such as glucaric acid, mannaric acid, gularic acid, idalic acid, etc.; and aldonic acids such as gluconic acid, galactonic acid, mannoic acid, talonic acid, allonic acid, etc., of which gluconic acid is especially preferred.

The non-toxic salts of these acids include, for example, salts thereof with alkali metals such as sodium or potassium, salts thereof with alkaline earth metals such as calcium or magnesium, and salts thereof with transition metals such as copper, iron or zinc, of which sodium gluconate and calcium gluconate are especially preferred.

The intramolecular ester compounds of the acids are, for example, lactone compounds. For example, mentioned are intramolecular ester compounds of gluconic acid, such as glucono delta lactone, glucono gamma lactone, of which glucono delta lactone is especially preferred.

These hexose-derived acids may be used alone or as an optional combination of two or more thereof.

As the short-chain fatty acids, may be mentioned fatty acids having two to four carbon atoms such as acetic acid, propionic acid, butyric acid, isobutyric acid, valeric acid, isovaleric acid, caprylic acid, etc. Lactic acid and succinic acid which differ from these acids in their intracorporeal absorption mechanism and in their influences on living bodies are not included within the scope of the short-chain fatty acids in the present invention.

The wording "improvement of feed efficiency" essentially means that even poorly-nutritious animal feed prepared from poor-quality cereals can attain almost the same level of fattening-promoting effect as that of highly-nutritious high-quality feed by addition of any of the hexose-derived acids thereto, but it also means that, when any of the hexose-derived acids is added to highly-nutritious feed, the feed attains a more elevated fattening-promoting effect.

The hexose-derived acids may be used as they are, but may be combined with solid or liquid vehicles well known in the art such as lactose, sucrose, glucose, corn starch, gelatin, starch, water, glycerin, fatty oil, sorbitol and the like to be used as agents for promoting the fattening of animals, agents for promoting the growth of animal enterobacteria, and agents for inhibiting the production of intracorporeal harmful substances.

These agents may be optionally mixed with ordinary additives such as antibacterial agents, antifungal agents, anthelminthics, antioxidants, dyes, flavorings, seasonings and enzymes, and may be prepared in the form of powders, dispersions, granules, liquid, tablets and the like by conventional methods.

The agents may be administered to animals as they are, or may be added to feed or drinking water to be taken by animals. Preferably, they are blended to feed or drinking water for animals.

The feed and drinking water may be any that is ordinary used, and is not particularly limited. Examples of the feed include corn, rice, barley, wheat, milo, soybean refuse, cereal bran, defatted rice bran, fish meal, skim milk, dry whey, oil, fat, alfalfa meal, northern-sea meal, soybean oil and fat, dried pure beef tallow, wheat flour, rapeseed oil and fat, feather meal, animal oil and fat, calcium phosphate, corn gluten meal, molasses, corn germ meal, calcium carbonate, tricalcium phosphate, sodium chloride, choline chloride, vitamins (vitamin A, vitamin $B_1$, vitamin $B_2$, vitamin $B_6$, vitamin $B_{12}$, vitamin D, vitamin E, calcium pantothenate, nicotinamide, folic acid, etc.), amino acids (lysine, methionine, etc.), minor inorganic salts (magnesium sulfate, iron sulfate, copper sulfate, zinc sulfate, potassium iodide, cobalt sulfate, etc.), living microorganisms, etc., which may be blended and prepared as appropriate.

The dose of the hexose-derived acids varies depending on the species and the body weight of animals to which they are applied, but generally falls between 20 and 1300 mg/kg/day, preferably between 20 and 600 mg/kg/day. In the case where the hexose-derived acids are added to the feed or drinking water for animals, the hexose-derived acids may generally be used as active ingredients in a proportion between 0.05 and 2.0% by weight ("%" is hereinafter % by weight), preferably between 0.1 and 1.0%.

The invention also provides a method for raising animals by administering an agent as mentioned above to animals or by feeding animals with feed or drinking water that contains the agent.

The method is applicable to any ordinary livestock including, for example, cattle, pigs, horses, sheep, goats, rabbits, minks, chickens, turkeys, domestic ducks, quails, wild ducks, soft-shelled turtles, frogs, lobsters, prawns, shrimps, yellowtails, sea breams, globefishes, eels, salmon, trout, horse mackerels, etc. It is preferably applied especially to cattle, pigs or chickens. An agents according to the invention and the feed or drinking water containing it may be administered or fed to these animals in ordinary manners.

Together with the agent of the invention, enterobacteria such as *Megasphaera* and *Mitsuokella* may be administered directly to animals, for example, in the form of a dry preparation. This is expected to further enhance the promotion of the growth of enterobacteria followed by the promotion of the fattening of animals.

EXAMPLES

The invention is described in more detail with reference to the following Examples, which, however, are not intended to restrict the scope of the invention.

Example 1

To a feed for pigs (Colomeal GS, a Nippai feed mixture for raising suckling-stage piglets, manufactured by Nippon Haigo Shiryo), added were 0.0625%, relative to the weight of the feed, of sodium gluconate.

Examples 2 to 5

To the feed for pigs (Colomeal GS, a Nippai feed mixture for raising suckling-stage piglets, manufactured by Nippon Haigo Shiryo), added were 0.125% (Example 2), 0.25% (Example 3), 0.5% (Example 4) and 1.0% (Example 5), relative to the weight of the feed, of sodium gluconate.

Comparative Example 1

The feed for pigs (Colomeal GS, a Nippai feed mixture for raising suckling-stage piglets, manufactured by Nippon Haigo Shiryo) itself was used as feed.

Comparative Example 2

To the feed for pigs (Colomeal GS, a Nichihai feed mixture for raising suckling-stage piglets, manufactured by Nippon Haigo Shiryo), added were 2%, relative to the weight of the feed, of fumaric acid (manufactured by Takeda Chemical Industries Ltd.).

Test Example 1

The feeds of Examples 1 to 5 and Comparative Examples 1 and 2 were fed to groups of piglets (about 35-day-old hybrid piglets), each group being composed of 4 piglets (2 male piglets and 2 female piglets), continuously for 4 weeks. At the start of the feeding test, on two weeks after the start of the test, and at the end of the test, that is, three times in all, the piglets were weighed individually, and an increase in the body weight was calculated for each group. In each group, checked was the feed intake during the period between the days on which the body weight was measured, and the feed conversion ratio was calculated from the overall body weight increase and the overall feed intake. The test was repeated 4 times, and the body weight increases and feed conversion ratios obtained 4 times were averaged for every group. The results are shown in the following Table 1 and FIG. 1.

TABLE 1

| | Amount of Sodium Gluconate Added (%) | Amount of Fumaric Acid Added (%) | Mean Body Weight Increase ± S.D. (index*) | Mean Feed Conversion Ratio ± S.D. (index*) |
|---|---|---|---|---|
| Example 1 | 0.0625 | — | 14.58 ± 2.42 (102) | 1.78 ± 0.07 (92) |
| Example 2 | 0.125 | — | 14.50 ± 1.95 (102) | 1.85 ± 0.10 (95) |
| Example 3 | 0.25 | — | 14.90 ± 1.87 (104) | 1.75 ± 0.05 (90) |
| Example 4 | 0.5 | — | 15.35 ± 2.26 (108) | 1.69 ± 0.16 (87) |
| Example 5 | 1.0 | — | 15.95 ± 2.97 (112) | 1.74 ± 0.15 (90) |
| Comp. Example 1 | 0 | — | 14.28 ± 2.04 (100) | 1.94 ± 0.12 (100) |
| Comp. Example 2 | — | 2.0 | 14.50 ± 2.16 (102) | 1.85 ± 0.06 (96) |

*Index based on Comparative Example 1 of 100.

As shown in the results, in the cases where the piglets were fed with the feeds that contained from 0.0625 to 1.0% of sodium gluconate, the body weight of the piglets increased by 2 to 12% and the feed efficiency improved by 5 to 13%, as compared with the cases of the piglets not having taken sodium gluconate.

Example 6

To a feed for piglets ("Kobuta Tonton", a feed mixture for raising piglets, manufactured by Nippon Haigo Shiryo), added were 0.5%, relative to the weight of the feed, of sodium gluconate.

Example 7

To the feed for piglets ("Kobuta Tonton", a feed mixture for raising piglets, manufactured by Nippon Haigo Shiryo), added were 0.5%, relative to the weight of the feed, of glucono delta lactone.

Example 8

To the feed for piglets ("Kobuta Tonton", a feed mixture for raising piglets, manufactured by Nippon Haigo Shiryo), added were 0.5%, relative to the weight of the feed, of calcium gluconate.

Example 9

Sodium gluconate was added to and dissolved in tap water, the amount of which was such that piglets drank up in 8 hours/day (9:00 to 17:00), in such an amount that sodium gluconate could be taken by test piglets in the same amount as taken when the feed contained 0.5% gluconate (200 mg/kg-body weight/day). During the other hours, tap water not containing sodium gluconate was given. This cycle was repeated.

Comparative Example 3

The feed for piglets ("Kobuta Tonton", a feed mixture for raising piglets, manufactured by Nippon Haigo Shiryo) itself was used as feed.

Test Example 2

The feeds of Examples 6 to 8 and Comparative Example 3 and the drinking water of Example 9 were fed to groups of piglets (about 2-month-old ter-hybrid piglets), each group being composed of 6 piglets (3 male piglets and 3 female piglets), continuously for 8 weeks. At the start of the feeding test, on two weeks, 4 weeks and 6 weeks after the start of the test, and at the end of the test, that is, five times in all, the piglets were weighed individually, and the body weight increase was calculated for every group.

In each group, checked was the feed intake during the period between the days on which the body weight was measured, and the feed conversion ratio was obtained from the overall body weight increase and the overall feed intake.

The test was repeated 3 times for Example 6, once for Example 7, once for Examples 8 and 9, and twice for Comparative Example 3, and the obtained body weight increases and feed conversion ratios were averaged for every group. The results are shown in Table 2.

TABLE 2

| | Type of Additive, Administration Mode, and Amount of Additive Added (%) | Mean Body Weight Increase (kg) (index*) | Mean Feed Conversion Ratio (index*) |
|---|---|---|---|
| Example 6 | sodium gluconate in feed, 0.5 | 38.7 (112) | 2.77 (92) |
| Example 7 | glucono delta lactone in feed, 0.5 | 40.8 (118) | 2.57 (86) |
| Example 8 | calcium gluconate in feed, 0.5 | 38.2 (110) | 2.75 (92) |
| Example 9 | sodium gluconate in drinking water, 0.5 | 38.2 (110) | 2.87 (96) |
| Comparative Example 3 | sodium gluconate in feed, 0 | 34.7 (100) | 3.00 (100) |

*Index based on Comparative Example 3 of 100.

As shown in Table 2, in the cases where the piglets were fed with the feeds or the drinking water that contained 0.5% of sodium gluconate, calcium gluconate and glucono delta lactone, the body weight of the piglets increased by 10 to 18% and the feed efficiency improved by 4 to 14%, as compared with the cases of the piglets not having taken the gluconic acid derivatives.

Example 10

To a standard test feed for chickens (SDB No. 1 and SDB No. 2, standard test feeds for broilers, manufactured by Nippon Haigo Shiryo), added were 0.5%, relative to the weight of the feed, of sodium gluconate.

Example 11

Since chickens drink water in an amount 3 to 4 times larger than the amount of the feed they take, 0.14% of sodium gluconate were added to tap water with respect to the weight of the tap water (the amount of sodium gluconate added thereto corresponds to 0.5% thereof added to feed).

Comparative Example 4

The standard test feed for chickens (SDB No. 1 and SDB No. 2, standard test feeds for broilers, manufactured by Nippon Haigo Shiryo) itself was used as feed. Of the standard test feed for broilers, SDB No. 1 (this is for the former stage in raising broilers) and SDB No. 2 (this is for the latter stage in raising broilers) both contained 0.1% of sodium gluconate.

Test Example 3

The feeds of Example 10 and Comparative Example 4 and the drinking water prepared in Example 11 were fed to groups of new born broiler chicks (Chunky), each group being composed of 50 chicks (25 male chicks and 25 female chicks), continuously for 8 weeks. At the start of the feeding test, on two weeks, 4 weeks and 6 weeks after the start of the test, and at the end of the test, that is, five times in all, the chicks were weighed individually, and an increase in the body weight was calculated for every group. In each group, checked was the feed intake during the period between the days on which the body weight was measured, and the feed conversion ratio was calculated from the overall body weight increase and the overall feed intake. The results are shown in Table 3.

TABLE 3

|  | Amount of Sodium Gluconate Added (%) | Mean Body Weight Increase (g) (index*) | Mean Feed Conversion Ratio (index*) |
|---|---|---|---|
| Example 10 | in feed, 0.5 | 2847 (110) | 2.05 (94) |
| Example 11 | in drinking water, 0.14 | 2597 (106) | 2.03 (94) |
| Comparative Example 4 | in feed, 0 | 2460 (100) | 2.17 (100) |

*Index based on Comparative Example 4 of 100.

As shown in Table 3, in the cases where the chicks were fed with the feed that contained from 0.5% of sodium gluconate and the drinking water that contained 0.14% of sodium gluconate, the body weight of the chicks increased by 6 to 10% and the feed efficiency improved by 6%, as compared with the cases of the chicks not having taken sodium gluconate.

Test Example 4

To a feed for latter artificial milk suckling-stage piglets (manufactured by Nippon Kagaku Shiryo Kyokai) and to a feed for raising piglets (manufactured by Nippon Kagaku Shiryo Kyokai), added were 0.05, 0.1, 0.25, 0.5 and 1.0%, relative to the weight of the feeds, of sodium gluconate.

The above-mentioned feeds were fed to groups of piglets (body weight: about 20 kg), each group being composed of 4 piglets (2 male piglets and 2 female piglets), continuously for 8 weeks (the feed for latter artificial milk for the former 2 weeks and the feed for raising piglets for the latter 6 weeks). During the period of the feeding test, each of the piglets was weighed every week, and an increase in the body weight was calculated for every group. In each group, checked was the feed intake during the period between the days on which the body weight was measured, and the feed conversion ratio was calculated.

Figure 2:
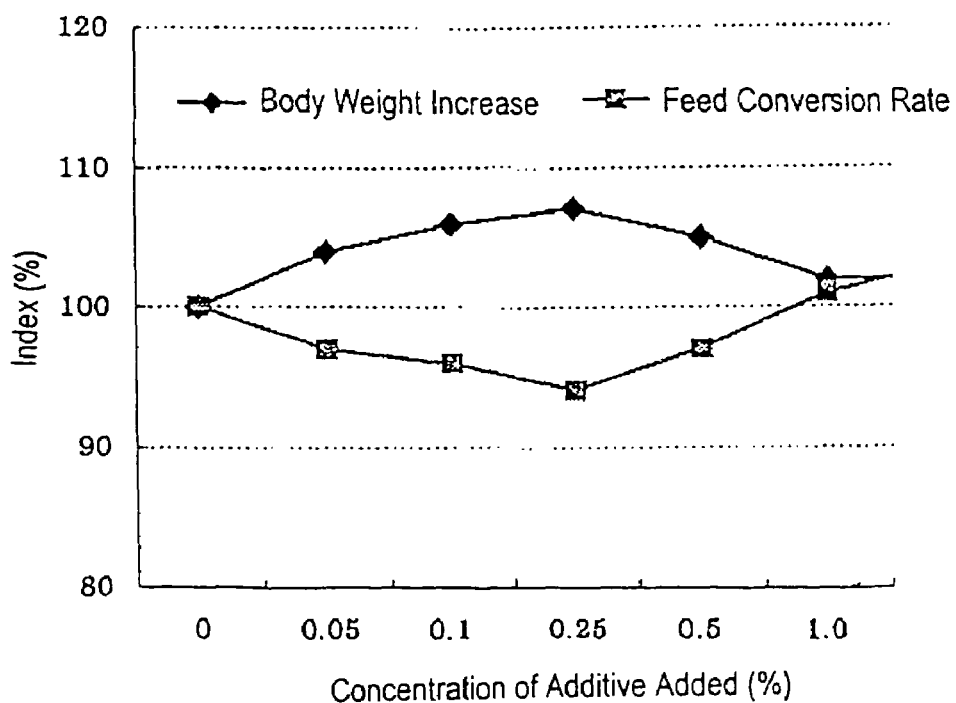
FIG. 2 is a graph showing the results of Test Example 4.

This test was repeated 10 times for the group not having taken sodium gluconate and the group having taken 0.5% sodium gluconate, but 5 times for the other groups having taken sodium gluconate in different concentrations. The obtained body weight increases and the feed conversion ratios were averaged for every group. The results are shown in Table 4 and FIG. 2.

TABLE 4

| Amount of Additive Added (%) | Test Cycle Frequency | Body Weight Increase (kg) ± S.D. (index %) | Feed Conversion Ratio ± S.D. (index %) |
|---|---|---|---|
| Control with no additive | — | 10 | 38.46 ± 4.44 (100) | 2.70 ± 0.14 (100) |
| Sodium Gluconate Added 0.05 | 5 | 39.96 ± 5.83 (104) | 2.62 ± 0.15 (97) |
| 0.1 | 5 | 40.92 ± 4.49 (106) | 2.58 ± 0.11 (96) |
| 0.25 | 5 | 41.26 ± 3.44 (107) | 2.55 ± 0.17 (94) |
| 0.5 | 10 | 40.43 ± 4.40 (105) | 2.63 ± 0.12 (97) |
| 1.0 | 5 | 39.28 ± 2.58 (102) | 2.74 ± 0.05 (101) |

As shown in the results, in the cases where the piglets were fed with the feeds containing 0.05 to 1.0 wt % of sodium gluconate, the body weight of the piglets increased by 2 to 7%, and the feed conversion ratio improved by 3 to 6%, as compared with the case where sodium gluconate was not added to the feeds.

Example 12

Three pigs were acclimated for 1 week, and the contents of their large intestines were taken out. The contents were diluted 5-fold with an anaerobic phosphate buffer (50 mM, pH 6.5), and then filtrated through 4-layered gauze. 25 mL of the resulting filtrate was put into serum bottles of 120 mL volume, and the gas phase therein was purged with a mixed gas of nitrogen/carbon dioxide (80/20). The bottles were sealed with butyl rubber stoppers and aluminum seals, and left for static culture at 39° C. for 24 hours (n=3).

Prior to putting the intestinal filtrate into the serum bottles, 1 w/v % glucose (positive control) and 1 w/v % sodium gluconate were put in the bottles, except for an additive-free control (negative control).

After the intestinal filtrate was thus cultivated, 1 mL of 6 N hydrochloric acid was added thereto to stop fermentation. The resulting cultures were analyzed as follows:

The cultures were pre-treated according to the Ushida and Sakata's conditions (Anim. Sci. Technol., 69, 571–575, 1988), and then were analyzed on the concentration of short-chain fatty acids, succinic acid and lactic acid therein by HPLC and the concentration of ammonia therein by the indophenol method (Weatherburn, Analytic Chem., 39, 971–974, 1967). Subtracting the concentration before cultivation from that after cultivation gives the amount (mM) generated through fermentation. The results are shown in Table 5.

TABLE 5

| | | Succinic Acid | Lactic Acid | Acetic Acid | Propionic Acid | Butyric Acid | Ammonia |
|---|---|---|---|---|---|---|---|
| Before Cultivation | | 0.17 (100) | 3.37 (100) | 40.06 (100) | 10.97 (100) | 5.39 (100) | 7.83 (100) |
| After Cultivation | Control with no additive | 0 (0) | 0.16 (5) | 69.27 (173) | 26.08 (238) | 8.97 (166) | 28.81 (368) |
| | Sodium Gluconate added | 0 (0) | 0 (0) | 161.90 (404) | 103.25 (941) | 70.36 (1305) | 5.79 (74) |

TABLE 5-continued

| | | | | | Propionic | | |
|---|---|---|---|---|---|---|---|
| | | Succinic Acid | Lactic Acid | Acetic Acid | Acid | Butyric Acid | Ammonia |
| | Glucose added | 1.26 (741) | 58.31 (173) | 119.04 (297) | 111.48 (1016) | 35.08 (651) | 4.82 (62) |

*The data parenthesized indicate the index based on the data before cultivation of 100.

As shown in Table 5, the concentration of acetic acid, propionic acid and butyric acid in the cultures with sodium gluconate added thereto greatly increased as compared with that in the cultures without sodium gluconate. This increase is comparable or higher as compared with the cultures with glucose added thereto, and in particular, butyric acid was observed to increase significant. Substances which may be harmful such as lactic acid, succinic acid and ammonia were observed to greatly reduce in the cultures with sodium gluconate added thereto.

Example 13

The amount of fermentation gas generated in the cultivation of Example 12 was measured by putting a glass syringe equipped with an injection needle into a head space of the serum bottle, sucking the gas until normal pressure is reached and measuring the sucked gas by a syringe scale.

The composition of the gas was analyzed for carbon dioxide, methane, hydrogen and hydrogen sulfide by TCD and FPD gas chromatography (Ushida, et al.; Jpn. J. Zootech. Sci., 53, 412–416, 1982, and Anim. Sci. Technol., 69, 571–575, 1998). The results are shown in Table 6 (n=3, μL/g).

TABLE 6

| | (μL/g) | | | | |
|---|---|---|---|---|---|
| | Total Gas | Carbon Dioxide | Hydrogen | Methane | Hydrogen Sulfide |
| Control with no additive | 2620 | 420 | 9.84 | 10 | 3.29 |
| Sodium Gluconate added | 6880 | 4330 | 211.99 | 30 | 0.09 |
| Glucose added | 4800 | 2180 | 228.53 | 0 | 0.29 |

As shown in Table 6, hydrogen sulfide, a harmful substance, greatly reduced in the cultures with sodium gluconate added thereto, as compared with the case of the cultures with no additives. The increased amount of generated hydrogen and methane suggests active anaerobic fermentation by microorganisms.

Example 14

Pigs were acclimated for 1 week, and the contents of their large intestines were taken out. The contents were diluted 5-fold with an anaerobic phosphate buffer (50 mM, pH 6.5), and then filtrated through 4-layered gauze. One mL of the resulting filtrate was inoculated on a PYF medium (100 mL) with 1 w/v % sodium gluconate added thereto, and incubated in an anaerobic condition at 39° C.

During incubation, 5 mL of a sterilized 10 w/v % aqueous solution of sodium gluconate were put into the medium at intervals of 48 hours.

The culture without sodium gluconate and the culture with sodium gluconate added thereto were sampled on 0, 8, 24, 48, 96 and 144 hours in a germ-free condition, and the samples were diluted to $10^{-5}$. 0.05 mL of each dilution were inoculated on BL agar media (manufactured by Nissui), and anaerobically incubated at 37° C. for 48 hours. The number of colonies of anaerobic microorganisms having grown in agar plates was counted (Table 7).

At the same time, according to the properties of the colonies thus grown, strains having grown only on the agar plate inoculated with the 144-hour sample of sodium gluconate-added culture were isolated, and they were counted and identified (Table 8).

TABLE 7

| | (data: logarithmic number of the cells in 1 g of culture) | | | | | |
|---|---|---|---|---|---|---|
| | Time after Start of Incubation (hrs) | | | | | |
| | 0 | 8 | 24 | 48 | 96 | 144 |
| Control with no additive | <6.3 | 8.3 | 9.3 | 8.3 | 8.4 | 7.4 |
| Sodium Gluconate added | <6.3 | 8.9 | 10.7 | 8.7 | 10.4 | 7.7 |

TABLE 8

| | (data: logarithmic number of the cells in 1 g of culture) | |
|---|---|---|
| | Control with no additive | Sodium Gluconate added |
| *Megasphaera elsdenii* | <6.3 | 6.4 |
| *Mitsuokella multiacidus* | <6.3 | 7.2 |

As shown in Tables 7 and 8, the addition of sodium gluconate increased the total number of anaerobic microorganisms. In particular, *Megasphaera elsdenii* and *Mitsuokella multiacidus* were observed to increase.

Example 15

The strains *Megasphaera elsdenii* and *Mitsuokella multiacidus* having grown in Example 14 were anaerobically incubated in PYF media (100 mL) with 1% w/v sodium gluconate added thereto, at 39° C. for 24 hours. The cultures were analyzed on the concentration of the short-chain fatty acids (mM) therein in the same manner as in Example 12. The results are shown in Table 9.

TABLE 9

| Type of Enterobacteria | | Acetic Acid | Propionic Acid | Butyric Acid |
|---|---|---|---|---|
| Megasphaera elsdenii | Control with no additive | 5.8 | 1.6 | 1.4 |
| | Sodium Gluconate added | 8.7 | 0.8 | 4.9 |
| | Difference | 2.9 | −0.8 | 3.5 |
| Mitsuokella multiacidus | Control with no additive | 2.9 | 7.0 | 0.3 |
| | Sodium Gluconate added | 9.9 | 43.1 | 1.0 |
| | Difference | 7.0 | 36.1 | 0.7 |

As shown in Table 9, it was confirmed that the two species of enterobacteria utilized sodium gluconate to produce various short-chain fatty acids. In particular, *Megasphaera elsdenii* produced a lot of acetic acid and butyric acid, and *Mitsuokella multiacidus* produced a lot of acetic acid and propionic acid.

The present invention provides an agent for promoting the fattening of animals, which contains, as the active ingredient, at least one of hexose-derived acids and their non-toxic salts and intramolecular ester compounds and also provides a method for promoting the fattening of animals by use of the promoting agent.

The promoting agent increases enterobacteria, thereby inducing the production only of short-chain fatty acids that are useful for the growth of living things. Consequently, even a poorly-nutritious feed can attain the same level of feed efficiency as that of highly-nutritious feed, and the fattening of animals can be promoted.

The invention claimed is:

1. The method for feeding an animal comprising:
administering to an animal a composition comprising an agent and a dried agent,
wherein said agent comprises at least one gluconic acid, a non-toxic salt of gluconic acid, or an intramolecular ester compound of a gluconic acid in an amount sufficient to promote the growth of enterobacteria, and
wherein said dried agent consists of *Megasphaera* and *Mitsuokella;*
wherein said non-toxic salt is an alkali metal salt or an alkaline earth metal salt, and wherein said intramolecular ester compound of gluconic acid is glucono delta lactone.

2. The method of claim 1, wherein said agent comprises sodium gluconate, calcium gluconate or glucono delta lactone.

3. The method of claim 1, wherein said enterobacteria are *Megasphaera* and *Mitsuokella*.

4. The method of claim 1, wherein said at least one gluconic acid, non-toxic salt thereof, or intramolecular ester thereof, is administered to an animal in an amount of 20 to 1300 mg/kg/day.

5. The method of claim 1, wherein said animal is selected from the group consisting of cattle, pigs and chickens.

6. The method of claim 1, which inhibits the production of an intracorporeal harmful substance in said animal.

7. An animal feed comprising an agent and a dried agent,
wherein said agent comprises at least one gluconic acid, a non-toxic alkali metal or alkaline earth metal salt of gluconic acid, or an intramolecular ester compound of a gluconic acid which is glucono delta lactone, in an amount sufficient to promote the growth of enterobacteria, and
wherein said dried agent consists of *Megasphaera* and *Mitsuokella*.

* * * * *